US00PP25401P2

(12) United States Plant Patent
Rijnbeek et al.

(10) Patent No.: US PP25,401 P2
(45) Date of Patent: Mar. 31, 2015

(54) ***AGAPANTHUS* PLANT NAMED 'MOONLIGHT STAR'**

(50) Latin Name: *Agapanthus africanus*
Varietal Denomination: Moonlight Star

(71) Applicants: Anthonius Phillipus Maria Rijnbeek, Boskoop (NL); Kitty de Jong, Roelofarendsveen (NL)

(72) Inventors: Anthonius Phillipus Maria Rijnbeek, Boskoop (NL); Kitty de Jong, Roelofarendsveen (NL)

(73) Assignee: Anthonius Phillipus Maria Rijnbeek, Boskoop (NL)

( * ) Notice: Subject to any disclaimer, the term of this patent is extended or adjusted under 35 U.S.C. 154(b) by 133 days.

(21) Appl. No.: 13/815,889

(22) Filed: Mar. 15, 2013

(51) Int. Cl.
*A01H 5/00* (2006.01)

(52) U.S. Cl.
USPC ..... Plt./398

(58) Field of Classification Search
USPC ..... Plt./398
See application file for complete search history.

*Primary Examiner* — Annette Para
(74) *Attorney, Agent, or Firm* — C. A. Whealy

(57) ABSTRACT

A new and distinct cultivar of *Agapanthus* plant named 'Moonlight Star', characterized by its upright and relatively compact plant habit; outwardly arching leaves; numerous star-shaped flowers with light and dark violet blue-striped flowers arranged on upright and strong scapes; and good garden performance.

2 Drawing Sheets

Botanical designation: *Agapanthus africanus.*
Cultivar denomination: 'MOONLIGHT STAR'.

BACKGROUND OF THE INVENTION

The present invention relates to a new and distinct cultivar of *Agapanthus* plant, botanically known as *Agapanthus africanus* and hereinafter referred to by the name 'Moonlight Star'.

The new *Agapanthus* plant is the result of a cross-pollination made by the Inventors in June, 1999 of two unnamed proprietary seedling selections of *Agapanthus africanus*, not patented. The new *Agapanthus* plant was discovered and selected by the Inventors as a single flowering plant from within the progeny of the stated cross-pollination grown in a controlled environment in Roelofarendsveen, The Netherlands in June, 2002.

Asexual reproduction of the new *Agapanthus* plant by divisions in a controlled environment in Roelofarendsveen, The Netherlands since February, 2003 has shown that the unique features of this new *Agapanthus* plant are stable and reproduced true to type in successive generations.

SUMMARY OF THE INVENTION

Plants of the new *Agapanthus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Moonlight Star'. These characteristics in combination distinguish 'Moonlight Star' as a new and distinct *Agapanthus* plant:

1. Upright and relatively compact plant habit.
2. Outwardly arching leaves.

3. Numerous star-shaped flowers with light and dark violet blue-striped flowers arranged on upright and strong scapes.
4. Good garden performance.

Plants of the new *Agapanthus* differ primarily from plants of the female parent selection in the following characteristics:

1. Plants of the new *Agapanthus* are more compact than plants of the female parent selection.
2. Plants of the new *Agapanthus* and the female parent selection differ in flower color.

Plants of the new *Agapanthus* differ primarily from plants of the male parent selection in the following characteristics:

1. Plants of the new *Agapanthus* are more compact than plants of the male parent selection.
2. Plants of the new *Agapanthus* and the male parent selection differ in flower color.

Plants of the new *Agapanthus* can be compared to plants of 'Blue Heaven', disclosed in U.S. Plant Pat. No. 14,989. In side-by-side comparisons conducted in Boskoop, The Netherlands, plants of the new *Agapanthus* and 'Blue Heaven' differed in the following characteristics:

1. Plants of the new *Agapanthus* were more compact than plants of 'Blue Heaven'.
2. Plants of the new *Agapanthus* and 'Blue Heaven' differed in flower color as plants of 'Blue Heaven' had violet blue-colored flowers.

BRIEF DESCRIPTION OF THE PHOTOGRAPHS

The accompanying colored photographs illustrate the overall appearance of the new *Agapanthus* plant showing the colors as true as it is reasonably possible to obtain in colored reproductions of this type. Colors in the photographs may differ slightly from the color values cited in the detailed botanical description which accurately describe the colors of the new *Agapanthus* plant.

The photograph on the first sheet comprises a top perspective view of a typical flowering plant of 'Moonlight Star' grown in a container.

The photograph at the top of the second sheet is a close-up view of a typical inflorescence of 'Moonlight Star'.

The photograph at the bottom of the second sheet is a close-up view of typical leaves of 'Moonlight Star'.

DETAILED BOTANICAL DESCRIPTION

The aforementioned photographs and following observations, measurements and values describe plants grown during the late spring and early summer in 17-cm containers in a greenhouse in Boskoop, The Netherlands and under cultural practices typical of commercial *Agapanthus* production. During the production of the plants, day temperatures ranged from 15° C. to 23° C. and night temperatures ranged from 8° C. to 16° C. Plants were two years old when the photographs and description were taken. In the following description, color references are made to The Royal Horticultural Society Colour Chart, 2007 Edition, except where general terms of ordinary dictionary significance are used.

Botanical classification: *Agapanthus africanus* 'Moonlight Star'.

Parentage:

*Female, or seed, parent*.—Unnamed proprietary seedling selection of *Agapanthus africanus*, not patented.

*Male, or pollen, parent*.—Unnamed proprietary seedling selection of *Agapanthus africanus*, not patented.

Propagation:

*Type*.—By tissue culture.

*Time to initiate roots, summer*.—About six weeks at temperatures about 18° C.

*Time to produce a rooted plant, summer*.—About 13 weeks at temperatures about 16° C.

*Root description*.—Medium in thickness, slightly fibrous; greyed white in color.

*Rooting habit*.—Moderate branching; medium density.

Plant description:

*Plant form and growth habit*.—Herbaceous flowering perennial plant; upright and relatively compact plant habit with outwardly arching leaves and strong upright flower scapes; leaves and flowering stems basal; moderately vigorous growth habit.

*Plant height* (*soil level to top of foliar plane*).—About 25.7 cm.

*Plant height* (*soil level to top of floral plane*).—About 63.5 cm.

*Plant width* (*spread*).—About 42 cm.

Foliage description:

*Arrangement and appearance*.—Leaves arranged in a basal rosette with about 16 leaves per rosette; leaves distichous, simple, sessile and outwardly arching.

*Leaf length*.—About 29.3 cm.

*Leaf width*.—About 2.2 cm.

*Shape*.—Linear-lanceolate.

*Apex*.—Broadly acute.

*Base*.—Cuneate.

*Margin*.—Entire.

*Texture, upper and lower surfaces*.—Smooth, glabrous; thick and leathery.

*Venation pattern*.—Parallel.

*Color*.—Developing leaves, upper surface: Close to between 143B and 144A. Developing leaves, lower surface: Close to between 143B and 144A to 144B. Fully expanded leaves, upper surface: Close to between 137B and 141A; venation, close to 143B. Fully expanded leaves, lower surface: Close to between 137B and 143A; venation, close to 143C.

Flower description:

*Flower type and flowering habit*.—Single star-shaped flowers arranged in terminal umbels supported by strong upright scapes; flowers face mostly outwardly to slightly upright; umbels roughly hemispherical in shape; freely flowering habit with about 65 flowers developing per umbel.

*Fragrance*.—Faint, somewhat musky.

*Natural flowering season*.—Plants being flowering about ten months after planting; flowering continuous from July to August in The Netherlands.

*Postproduction longevity*.—Flowers last about one week the plant; flowers not persistent.

*Flower buds*.—Height: About 2.6 cm. Diameter: About 8 mm. Shape: Obovate. Color: Close to N89C; towards the base, close to 92A to 92D.

*Inflorescence height*.—About 11 cm.

*Inflorescence diameter*.—About 15.7 cm.

*Flower diameter*.—About 5.7 cm.

*Flower depth*.—About 4.5 cm.

*Perianth*.—Quantity and arrangement: Typically six to eight segments arranged in two whorls; lower 25% of the segments are fused into a narrow tube; upper free part of segments flaring outwardly. Segment length: About 3.9 cm. Segment width: About 8 mm to 11 mm. Segment lobe shape: Narrowly obovate. Segment apex: Broadly acute. Segment margin: Entire, undulate. Segment texture, upper and lower surfaces: Smooth, glabrous. Segment color: When opening, upper surface: Close to between 92B to 94D; margins and central longitudinal stripe, close to N89B to N89C. When opening, lower surface: Close to 93C; margins and central longitudinal stripe, close to N89C. Fully opened, upper surface: Close to 94C; towards the base, close to 92B; margins, close to N89D; central longitudinal stripe, close to N89B; color becoming closer to 84A with development. Fully opened, lower surface: Close to 93C; margins and central longitudinal stripe, close to N89C.

*Peduncles* (*scapes*).—Length: About 52.3 cm. Diameter: About 5 mm to 9 mm. Aspect: Upright. Strength: Strong. Texture: Smooth, glabrous. Color: Close to 143A; towards the base, close to 143A to 143B.

*Pedicels*.—Length: About 4 mm. Diameter: About 2 mm. Aspect: Upright to horizontal from the peduncle axis. Strength: Strong. Texture: Smooth, glabrous. Color: Close to 143A; distally, upper surface tinged with close to 203A.

*Reproductive organs*.—Stamens: Quantity per flower: Typically six. Filament length: About 3 cm. Filament color: Close to 94C; towards the base, close to 92D. Anther shape: Narrowly oblong; dorsifixed. Anther length: About 4 mm. Anther color: Close to N186B. Pollen amount: Moderate. Pollen color: Close to 195A. Pistils: Quantity per flower: One. Pistil length: About 2.5 cm. Style length: About 2.45 cm. Style color: Close to 94C; towards the base, close to 92D. Stigma shape: Narrowly clavate. Stigma color: Close to 94B to 94C. Ovary color: Close to 154D.

*Seeds and fruits*.—Seed and fruit development have not been observed on plants of the new *Agapanthus*.

Disease & pest resistance: Plants of the new *Agapanthus* have not been noted to be resistant to pathogens and pests common to *Agapanthus* plants.

Garden performance: Plants of the new *Agapanthus* have been observed to have good garden performance and to tolerate rain, wind, high temperatures about 40° C. and to be hardy to USDA Hardiness Zone 8.

It is claimed:

1. A new and distinct *Agapanthus* plant named 'Moonlight Star' as illustrated and described.

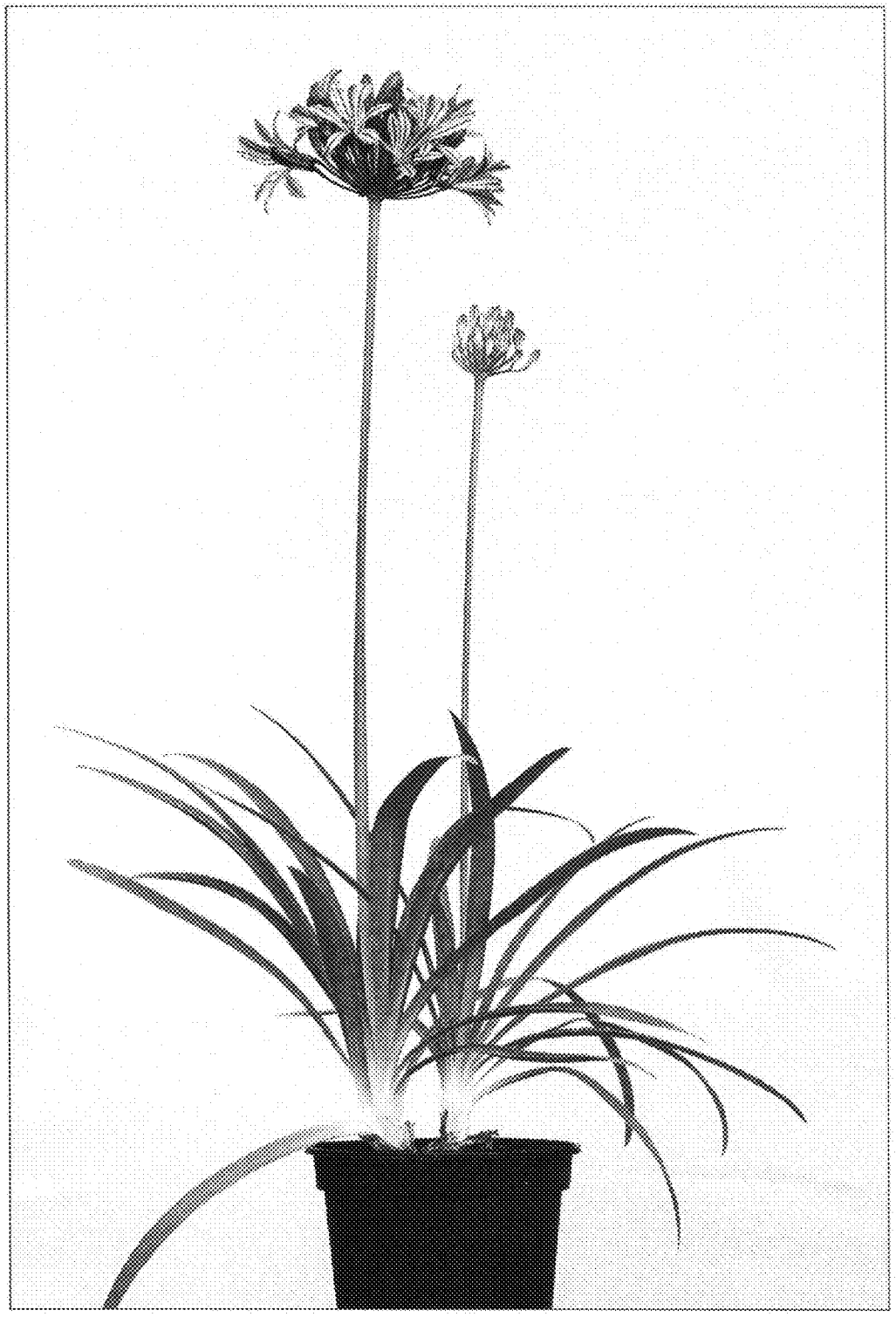

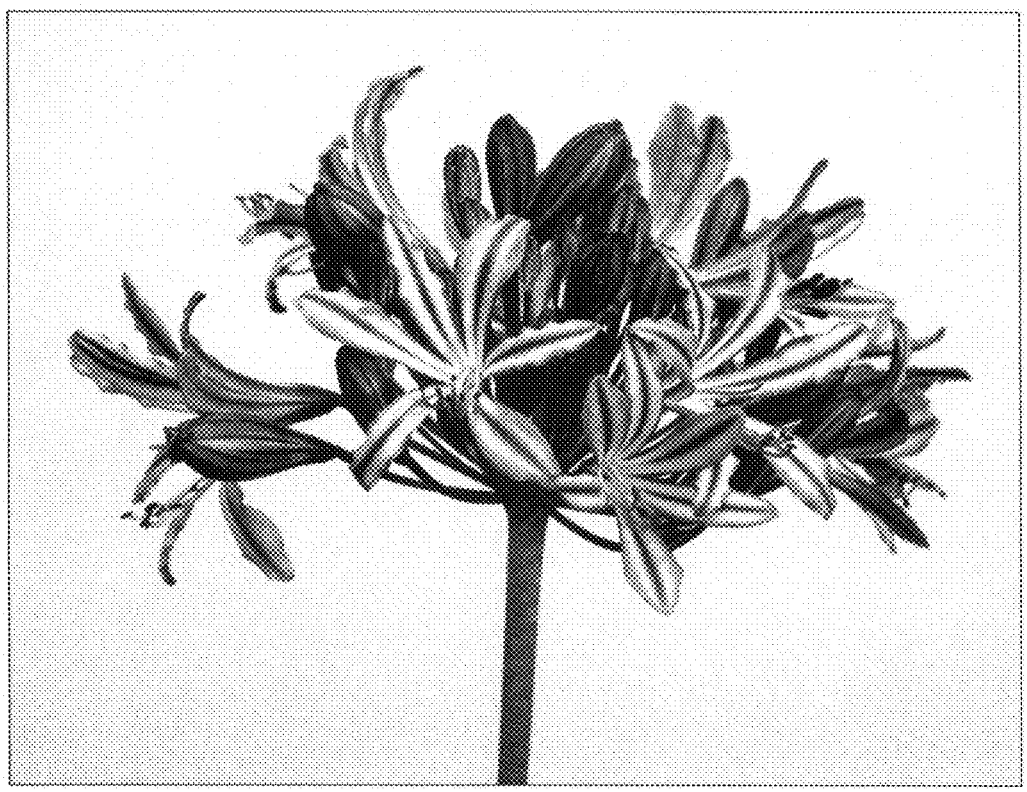
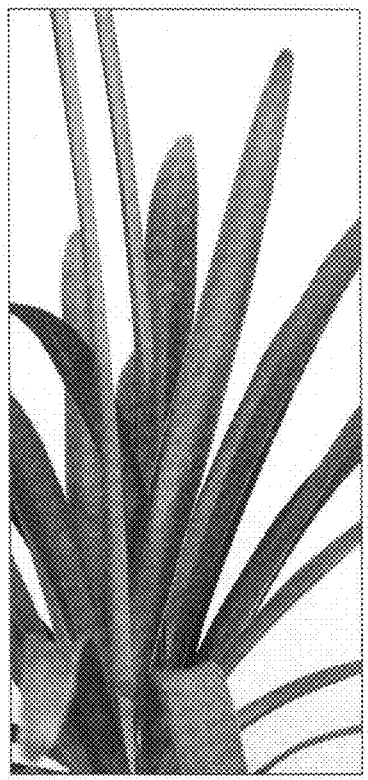

* * * * *